(12) United States Patent
Zheng et al.

(10) Patent No.: US 12,379,347 B2
(45) Date of Patent: Aug. 5, 2025

(54) METHOD FOR IN-SITU U-Pb DATING OF HETEROGENEOUS MINERALS

(71) Applicants: Zijin Mining Group Co., Ltd., Longyan (CN); CHINA UNIVERSITY OF GEOSCIENCES (WUHAN), Wuhan (CN)

(72) Inventors: Youye Zheng, Wuhan (CN); Shouhong Lin, Wuhan (CN); Changshun Jia, Wuhan (CN); Xiaodan Lai, Wuhan (CN); Xu Kang, Wuhan (CN); Jinzhang Zhang, Wuhan (CN); Rongzhu Guan, Wuhan (CN); Xiaojia Jiang, Wuhan (CN); Xin Chen, Wuhan (CN)

(73) Assignees: Zijin Mining Group Co., Ltd., Longyan (CN); CHINA UNIVERSITY OF GEOSCIENCES (WUHAN), Wuhan (CN)

( * ) Notice: Subject to any disclaimer, the term of this patent is extended or adjusted under 35 U.S.C. 154(b) by 228 days.

(21) Appl. No.: 18/451,850

(22) Filed: Aug. 18, 2023

(65) Prior Publication Data
US 2024/0319137 A1    Sep. 26, 2024

(30) Foreign Application Priority Data

Mar. 24, 2023    (CN) .......................... 202310413831.0

(51) Int. Cl.
*G01N 27/62*    (2021.01)
*G01N 33/24*    (2006.01)

(52) U.S. Cl.
CPC ............. *G01N 27/62* (2013.01); *G01N 33/24* (2013.01); *G01N 2223/01* (2013.01); *G01N 2223/073* (2013.01)

(58) Field of Classification Search
CPC ...... G01N 27/62; G01N 27/628; G01N 33/24; G01N 1/08; G01N 21/84; G01N 2223/01; G01N 2223/073; G06F 18/23213; G06F 18/24; Y02P 10/20
See application file for complete search history.

(56) References Cited

U.S. PATENT DOCUMENTS

| 7,337,684 | B1 | 3/2008 | Lewis |
| 10,473,559 | B2 | 11/2019 | Case |
| 10,481,048 | B2 | 11/2019 | Giles |

*Primary Examiner* — Jurie Yun
(74) *Attorney, Agent, or Firm* — True Shepherd LLC; Andrew C. Cheng

(57) ABSTRACT

In a method for in-situ U-Pb dating of heterogeneous minerals, a target mineral is separated and purified by carrying out data analysis, extraction and enhancement on original mapping data. The method highlights distribution features of dating indexes (U content, Pb content, $Pb^{206}/U^{238}$ ratio, $Pb^{207}/U^{235}$ ratio and Th/U ratio) in a target mineral phase with a noise data processing technology, and more intuitively displays a favorable dating portion and a crystal growth change trend of the dating mineral. Further, a fine spot design is provided for high-precision dating analysis in a later stage. A plurality of geological events experienced by a heterogeneous mineral crystal in a growth process is accurately limited, so as to invert the mineral formation history which provides the basis for better study of mineralogy, mineral geochemistry and mineral geochronology. It is hence a novel indispensable auxiliary means of mineral geochronology and an auxiliary method for mineral exploration.

8 Claims, 15 Drawing Sheets

| No. | Content (ppm) | | Ratio | | | | | | | | Age (Ma) | | | | | |
|---|---|---|---|---|---|---|---|---|---|---|---|---|---|---|---|---|
| | Pb | U | $^{207}Pb/^{206}Pb$ | 2σ | $^{207}Pb/^{235}U$ | 2σ | $^{206}Pb/^{238}U$ | 2σ | $^{207}Pb/^{206}Pb$ | 2σ | $^{207}Pb/^{235}U$ | 2σ | $^{206}Pb/^{238}U$ | 2σ | | |

Relatively low-U rutile

| No. | Pb | U | $^{207}Pb/^{206}Pb$ | 2σ | $^{207}Pb/^{235}U$ | 2σ | $^{206}Pb/^{238}U$ | 2σ | Age1 | 2σ | Age2 | 2σ | Age3 | 2σ |
|---|---|---|---|---|---|---|---|---|---|---|---|---|---|---|
| 1-1-01 | 1.19 | 10.3 | 0.0645 | 0.0180 | 0.5152 | 0.0558 | 0.0677 | 0.0027 | 767 | 339 | 422 | 37 | 422 | 16 |
| 1-1-02 | 0.55 | 10.4 | 0.072 | 0.0126 | 0.599 | 0.0733 | 0.0677 | 0.0038 | 987 | 358 | 477 | 48 | 422 | 23 |
| 1-1-03 | 0.61 | 10.5 | 0.0839 | 0.0138 | 0.7465 | 0.0733 | 0.0694 | 0.0031 | 1336 | 317 | 566 | 43 | 433 | 19 |
| 1-1-04 | 0.97 | 10.3 | 0.0433 | 0.0078 | 0.4321 | 0.0523 | 0.0701 | 0.0036 | | | 365 | 37 | 437 | 16 |
| 1-1-05 | 1.06 | 9.9 | 0.0655 | 0.0091 | 0.5681 | 0.0537 | 0.068 | 0.0036 | 791 | 299 | 457 | 35 | 424 | 16 |
| 1-1-06 | 0.39 | 10.6 | 0.0601 | 0.0182 | 0.5205 | 0.0442 | 0.0688 | 0.0028 | 606 | 373 | 425 | 29 | 429 | 15 |
| 1-1-07 | 1.03 | 10.5 | 0.06 | 0.0143 | 0.4809 | 0.0695 | 0.0681 | 0.004 | 611 | 437 | 399 | 48 | 434 | 24 |
| 1-1-08 | 1 | 10.2 | 0.0672 | 0.0096 | 0.5538 | 0.0542 | 0.0682 | 0.0034 | 843 | 297 | 448 | 33 | 423 | 21 |
| 1-1-09 | 0.53 | 9.6 | 0.0605 | 0.0097 | 0.4909 | 0.0543 | 0.0677 | 0.0032 | 620 | 388 | 405 | 37 | 422 | 19 |
| 1-1-10 | 0.64 | 10 | 0.0653 | 0.0125 | 0.5168 | 0.0623 | 0.0682 | 0.0036 | 789 | 408 | 423 | 42 | 426 | 16 |
| 1-1-11 | 0.55 | 10 | 0.0963 | 0.0191 | 0.8664 | 0.0539 | 0.0703 | 0.0033 | 1558 | 363 | 519 | 36 | 438 | 20 |
| 1-1-12 | 0.53 | 10.3 | 0.0643 | 0.0181 | 0.5133 | 0.0523 | 0.0669 | 0.0028 | 734 | 333 | 421 | 33 | 418 | 17 |
| 1-1-13 | 1.44 | 9.3 | 0.0533 | 0.0096 | 0.5838 | 0.0828 | 0.0683 | 0.0028 | 433 | 339 | 414 | 36 | 427 | 17 |
| 1-1-14 | 0.79 | 10.1 | 0.05 | 0.0089 | 0.4223 | 0.0581 | 0.0678 | 0.0029 | 195 | 367 | 358 | 36 | 423 | 18 |
| 1-1-15 | 0.63 | 9.8 | 0.0549 | 0.0135 | 0.5006 | 0.0676 | 0.0683 | 0.0036 | 409 | 474 | 412 | 46 | 426 | 22 |
| 1-1-16 | 0.9 | 9.6 | 0.0564 | 0.011 | 0.5434 | 0.0713 | 0.0692 | 0.0033 | 478 | 372 | 440 | 47 | 432 | 21 |
| 1-1-17 | 0.61 | 10.6 | 0.0735 | 0.0148 | 0.5589 | 0.0636 | 0.0681 | 0.0025 | 1083 | 400 | 448 | 42 | 425 | 15 |

Relatively high-U rutile

| No. | Pb | U | $^{207}Pb/^{206}Pb$ | 2σ | $^{207}Pb/^{235}U$ | 2σ | $^{206}Pb/^{238}U$ | 2σ | Age1 | 2σ | Age2 | 2σ | Age3 | 2σ |
|---|---|---|---|---|---|---|---|---|---|---|---|---|---|---|
| 1-2-01 | 1.9 | 36.3 | 0.0527 | 0.0053 | 0.4861 | 0.0446 | 0.0679 | 0.0015 | 317 | 227 | 402 | 30 | 424 | 9 |
| 1-2-02 | 3.03 | 25.1 | 0.073 | 0.008 | 0.685 | 0.0634 | 0.0691 | 0.0019 | 1133 | 217 | 530 | 39 | 431 | 11 |
| 1-2-03 | 1.98 | 30.2 | 0.0488 | 0.0064 | 0.4608 | 0.0478 | 0.0713 | 0.002 | 178 | 278 | 385 | 33 | 443 | 12 |
| 1-2-04 | 2.09 | 34.8 | 0.0627 | 0.0057 | 0.6203 | 0.0524 | 0.0709 | 0.0034 | 698 | 190 | 490 | 33 | 441 | 14 |
| 1-2-05 | 2.81 | 34.6 | 0.06 | 0.0075 | 0.5284 | 0.0557 | 0.0674 | 0.0022 | 606 | 272 | 431 | 37 | 420 | 13 |
| 1-2-06 | 2.38 | 40.5 | 0.0446 | 0.0041 | 0.4175 | 0.032 | 0.0688 | 0.0014 | | | 354 | 23 | 429 | 8 |
| 1-2-07 | 2.14 | 40.5 | 0.0552 | 0.0055 | 0.5168 | 0.0405 | 0.0683 | 0.0017 | 420 | 221 | 423 | 27 | 436 | 10 |
| 1-2-08 | 5.97 | 38.3 | 0.0789 | 0.0049 | 0.6918 | 0.0412 | 0.0721 | 0.0015 | 954 | 142 | 534 | 25 | 449 | 9 |
| 1-2-09 | 11.11 | 37.4 | 0.059 | 0.0063 | 0.5551 | 0.0493 | 0.0688 | 0.0017 | 565 | 231 | 448 | 32 | 428 | 10 |
| 1-2-10 | 3.1 | 48.1 | 0.054 | 0.0044 | 0.3922 | 0.0388 | 0.068 | 0.0012 | 372 | 177 | 413 | 26 | 424 | 7 |
| 1-2-11 | 2.88 | 40.6 | 0.0571 | 0.0047 | 0.5257 | 0.0385 | 0.0683 | 0.0019 | 494 | 180 | 429 | 26 | 426 | 13 |
| 1-2-12 | 2.45 | 47.4 | 0.0511 | 0.0041 | 0.4742 | 0.0339 | 0.0683 | 0.0017 | 336 | 183 | 394 | 25 | 426 | 10 |
| 1-2-13 | 3.62 | 38.2 | 0.0598 | 0.0053 | 0.5433 | 0.0412 | 0.0682 | 0.0017 | 587 | 194 | 441 | 37 | 425 | 10 |
| 1-2-14 | 3.13 | 31.9 | 0.054 | 0.0059 | 0.5112 | 0.0506 | 0.069 | 0.0018 | 372 | 246 | 419 | 34 | 430 | 11 |
| 1-2-15 | 2.86 | 45.4 | 0.0571 | 0.0038 | 0.528 | 0.0305 | 0.0681 | 0.0014 | 494 | 144 | 431 | 20 | 425 | 8 |
| 1-2-16 | 2.28 | 42.3 | 0.0594 | 0.0048 | 0.5501 | 0.0347 | 0.0683 | 0.0018 | 583 | 175 | 445 | 27 | 426 | 10 |
| 1-2-17 | 1.79 | 27.6 | 0.0611 | 0.0074 | 0.5498 | 0.0543 | 0.0687 | 0.002 | 643 | 259 | 445 | 36 | 428 | 12 |
| 1-2-18 | 3.57 | 43.1 | 0.0611 | 0.0043 | 0.568 | 0.0363 | 0.0682 | 0.0014 | 643 | 142 | 457 | 34 | 425 | 8 |
| 1-2-19 | 2.84 | 32.9 | 0.0631 | 0.0037 | 0.5831 | 0.0332 | 0.0689 | 0.0015 | 676 | 127 | 466 | 21 | 430 | 9 |
| 1-2-20 | 3.43 | 33.3 | 0.0735 | 0.0063 | 0.6522 | 0.0491 | 0.0688 | 0.0021 | 1028 | 168 | 510 | 27 | 428 | 13 |
| 1-2-21 | 2.33 | 41.1 | 0.0603 | 0.0044 | 0.5557 | 0.0344 | 0.0681 | 0.0014 | 617 | 157 | 449 | 22 | 425 | 8 |
| 1-2-22 | 2.79 | 55 | 0.0556 | 0.0059 | 0.5267 | 0.0539 | 0.0681 | 0.0033 | 439 | 234 | 430 | 37 | 425 | 20 |

FIG.6

| | Content (ppm) | | | | Ratio | | | | | | Age (Ma) | | | | | |
|---|---|---|---|---|---|---|---|---|---|---|---|---|---|---|---|---|
| | Pb | Th | U | Th/U | $^{207}Pb/^{206}Pb$ | 1σ | $^{207}Pb/^{235}U$ | 2σ | $^{206}Pb/^{238}U$ | 2σ | $^{207}Pb/^{206}Pb$ | 2σ | $^{207}Pb/^{235}U$ | 2σ | $^{206}Pb/^{238}U$ | 2σ |
| Zircon | | | | | | | | | | | | | | | | |
| Edge | | | | | | | | | | | | | | | | |
| 1-1 | 340.6 | 46 | 4710.4 | 0.01 | 0.05692 | 0.00108 | 0.52788 | 0.01001 | 0.06815 | 0.00073 | 469 | 49 | 430 | 7 | 425 | 4 |
| 1-2 | 237.8 | 57.3 | 3297 | 0.017 | 0.05411 | 0.00114 | 0.51272 | 0.01141 | 0.06824 | 0.00088 | 376 | 32 | 420 | 8 | 426 | 4 |
| 1-3 | 143.8 | 27.9 | 1947.3 | 0.014 | 0.05462 | 0.00118 | 0.51663 | 0.01213 | 0.06829 | 0.0008 | 397 | 32 | 423 | 8 | 426 | 5 |
| 1-4 | 338.3 | 47.2 | 4738.4 | 0.01 | 0.05398 | 0.00101 | 0.50984 | 0.00983 | 0.06828 | 0.00072 | 370 | 25 | 418 | 7 | 426 | 4 |
| 1-5 | 142.8 | 39.6 | 2011.1 | 0.019 | 0.05655 | 0.00112 | 0.53799 | 0.01095 | 0.06875 | 0.00071 | 474 | 27 | 437 | 7 | 429 | 4 |
| 1-6 | 203 | 56.8 | 2868.5 | 0.02 | 0.06168 | 0.00248 | 0.58907 | 0.02158 | 0.06878 | 0.001 | 605 | 90 | 457 | 14 | 429 | 6 |
| 1-7 | 219.5 | 79.4 | 3068.5 | 0.026 | 0.06032 | 0.0013 | 0.54342 | 0.01244 | 0.06894 | 0.00063 | 527 | 35 | 441 | 8 | 424 | 4 |
| 1-8 | 271.3 | 53.6 | 3839.2 | 0.014 | 0.05652 | 0.00131 | 0.5339 | 0.01153 | 0.06829 | 0.00065 | 473 | 31 | 436 | 8 | 426 | 4 |
| 1-9 | 97.8 | 24.2 | 1370.6 | 0.017 | 0.05614 | 0.00129 | 0.53216 | 0.01271 | 0.06829 | 0.00071 | 458 | 34 | 433 | 8 | 428 | 4 |
| 1-10 | 98.8 | 23.7 | 1384.5 | 0.017 | 0.05849 | 0.00143 | 0.53433 | 0.01364 | 0.06811 | 0.00073 | 488 | 62 | 435 | 9 | 425 | 4 |
| 1-11 | 248 | 69.8 | 3494.1 | 0.02 | 0.05769 | 0.00118 | 0.54051 | 0.01114 | 0.06812 | 0.00069 | 513 | 32 | 439 | 7 | 425 | 4 |
| 1-12 | 330.3 | 57.7 | 4630.5 | 0.008 | 0.05736 | 0.00106 | 0.5468 | 0.0102 | 0.06878 | 0.0007 | 505 | 24 | 443 | 7 | 429 | 4 |
| Core | | | | | | | | | | | | | | | | |
| 1-13 | 101.2 | 21.4 | 1387 | 0.015 | 0.05427 | 0.00131 | 0.52913 | 0.01282 | 0.07044 | 0.00082 | 383 | 54 | 431 | 9 | 439 | 5 |
| 1-14 | 222.8 | 16.8 | 3992.6 | 0.005 | 0.05355 | 0.00106 | 0.52285 | 0.01049 | 0.07048 | 0.00057 | 354 | 44 | 427 | 7 | 439 | 3 |
| 1-15 | 284 | 35.3 | 3793.5 | 0.009 | 0.05586 | 0.00117 | 0.54301 | 0.01191 | 0.07046 | 0.00065 | 439 | 46 | 440 | 8 | 439 | 4 |
| 1-16 | 204.1 | 13.3 | 2787.6 | 0.005 | 0.05488 | 0.00113 | 0.53373 | 0.01171 | 0.07024 | 0.00071 | 406 | 46 | 434 | 8 | 438 | 4 |
| 1-17 | 242 | 20.9 | 3293.7 | 0.006 | 0.05372 | 0.00094 | 0.52429 | 0.00978 | 0.07039 | 0.00058 | 367 | 39 | 428 | 7 | 439 | 4 |
| 1-18 | 120.1 | 25.6 | 1634.4 | 0.015 | 0.05338 | 0.00129 | 0.5208 | 0.01292 | 0.07035 | 0.00071 | 346 | 49 | 426 | 9 | 438 | 4 |
| 1-19 | 92.7 | 19 | 1294.1 | 0.015 | 0.05338 | 0.00125 | 0.52015 | 0.01241 | 0.07038 | 0.00068 | 346 | 49 | 425 | 8 | 438 | 4 |
| 1-20 | 254.4 | 27.3 | 3564.2 | 0.008 | 0.05544 | 0.00109 | 0.54143 | 0.01153 | 0.07046 | 0.00078 | 432 | 43 | 439 | 8 | 439 | 5 |
| 1-21 | 288.5 | 27.4 | 4034 | 0.007 | 0.05457 | 0.00102 | 0.53198 | 0.01064 | 0.07034 | 0.0007 | 394 | 41 | 433 | 7 | 438 | 4 |
| 1-22 | 35.9 | 7.8 | 497.2 | 0.016 | 0.05645 | 0.00171 | 0.54992 | 0.01784 | 0.07034 | 0.00096 | 478 | 67 | 445 | 12 | 438 | 6 |
| 1-23 | 123.4 | 27 | 1699.3 | 0.016 | 0.05563 | 0.00118 | 0.54284 | 0.01225 | 0.07037 | 0.00073 | 439 | 46 | 440 | 8 | 438 | 4 |
| 1-24 | 250.6 | 38 | 3508.5 | 0.011 | 0.05513 | 0.00107 | 0.53685 | 0.01087 | 0.07033 | 0.00074 | 417 | 44 | 436 | 7 | 438 | 4 |
| 1-25 | 204.5 | 53.8 | 2781.8 | 0.019 | 0.05534 | 0.00121 | 0.54353 | 0.01223 | 0.07088 | 0.0007 | 433 | 48 | 441 | 8 | 441 | 4 |
| 1-26 | 242.3 | 41.5 | 3333.4 | 0.012 | 0.05545 | 0.00103 | 0.54148 | 0.01063 | 0.07042 | 0.00066 | 432 | 43 | 439 | 7 | 439 | 4 |
| 1-27 | 327.5 | 85.1 | 4458.5 | 0.019 | 0.05681 | 0.00113 | 0.55401 | 0.01037 | 0.0704 | 0.00068 | 483 | 44 | 448 | 7 | 439 | 4 |
| 1-28 | 218.9 | 15.8 | 3035.7 | 0.005 | 0.0562 | 0.00107 | 0.549 | 0.01109 | 0.07043 | 0.00072 | 461 | 43 | 444 | 7 | 439 | 4 |

FIG. 14

METHOD FOR IN-SITU U-Pb DATING OF HETEROGENEOUS MINERALS

CROSS-REFERENCE TO RELATED APPLICATIONS

This application claims priority to Chinese Patent Application No. 202310413831.0 with a filing date of Mar. 24, 2023. The content of the aforementioned application, including any intervening amendments thereto, is incorporated herein by reference.

TECHNICAL FIELD

The present disclosure belongs to the technical field of mineral evolution, and particularly relates to a method for in-situ U-Pb dating of heterogeneous minerals.

BACKGROUND

Accurate measurement on the formation age of a geological body is indispensable for understanding its formation history in geological study. However, the geological body is affected by various internal and external factors during or after formation, resulting in changes in compositional heterogeneity of a mineral crystal. For example, changes in element contents and a U-Pb isotope system of the mineral will be affected by processes such as diffusion, recrystallization, secondary growth and corrosion precipitation. As a result, how to accurately determine the geological significance represented by the U-Pb isotope on a submicron scale in the mineral is crucial to restoration of an evolution history of the geological body.

With the progress of in-situ analysis technology, Laser Ablation Inductively Coupled Plasma Mass Spectrometry (LA-ICP-MS) plays an important role in in-situ geochronology due to its features of simplicity, convenience, rapidness and low operation cost. However, the randomness and blindness of LA-ICP-MS spot analysis makes it difficult to accurately determine a formation process of a highly heterogeneous sample, and leads to loss of important geochronology information. Spatial distribution of elements and isotopic compositions can help understand the growth process and formation history of the mineral, and is also beneficial for determining whether multiple stages and multi-secondary growth exist. Currently, more scholars have started to conduct mapping analysis of the mineral with LA-ICP-MS, through which distribution of elements and isotopes on a surface of the mineral can be well obtained. However, the mapping analysis is still defective for its shallow ablation depth, short ablation time, short analysis time as well as low precision compared with LA-ICP-MS spot analysis. Further, noise data, such as negative values and null values, will be generated during signal collection and testing. Moreover, interference in the test result of the mineral will be produced since the paragenetic mineral, the fracture and the inclusion of the mineral to be tested will be analyzed during the mapping analysis.

Accordingly, it is necessary to propose a novel, efficient, and suitable method for in-situ U-Pb dating of uranium-bearing heterogeneous minerals. The method should both have high precision in spot analysis, and well reflect spatial distribution of mineral elements and isotopes. In this way, the mineral formation history can be inverted accurately to provide important limitations for formation and evolution of the geological body.

SUMMARY OF PRESENT INVENTION

In view of the above defects in the prior art, the objective of the present disclosure is to provide a method for in-situ U-Pb dating of heterogeneous minerals.

In order to achieve the above objective, the present disclosure adopts the following technical solutions:

The present disclosure provides a method for in-situ U-Pb dating of heterogeneous minerals. The method includes the following steps:

S1, collecting a bedrock sample, where the bedrock sample is rich in any one of zircon, rutile or garnet;

S2, carrying out petrographic analysis of the sample which comprises the following sub-steps:

S21, grinding the collected bedrock sample into a probe piece having a width of 25 mm, a length of 30 mm-35 mm and a thickness of 0.05 mm and a laser sheet having a width of 25 mm, a length of 30 mm-35 mm and a thickness of 0.08 mm, microscopically observing mineral features corresponding to the probe piece and the laser sheet, and recording petrography and paragenetic association features of the probe piece and the laser sheet;

S22, selecting a single mineral crystal having a desirable crystal form, complete particles and no impurity inclusion as a representative sample; and S23, designing a rectangular area greater than a particle size of the single mineral crystal as an experimental test location with the single mineral crystal as a target on the bedrock sample, marking the rectangular area with a marking pen, and carrying out in-situ element mapping analysis on the selected experimental test location by a laser ablation inductively coupled plasma mass spectrometer;

S3, carrying out mineral phase separation and purification based on mapping data, which comprises the following sub-steps:

Classifying matrix data of LA-ICP-MS mapping obtained in step S23 by K-means semi-automatic supervised multi-channel classification, and hence achieving mineral phase separation to purify the single mineral crystal;

S4, carrying out data cleaning and filtering analysis, which comprises the following sub-steps:

for high-U minerals, carrying out data cleaning with purified and separated high-U mineral data, and replacing negative numbers and null values to carry out median filtering on processed data, so as to highlight an element distribution law; and for low-U minerals, carrying out data cleaning with purified and separated low-U mineral data, replacing negative values and null values to carry out median filtering on processed data, and determining a compositional zonation having high $U^{238}$ and low $Pb^{204}$, S5, carrying out stage determination and spot design, which comprises the following sub-steps:

for the high-U minerals, drafting a U-Pb concordia diagram with filtered data, determining whether multiple stages and Pb loss exist, computing a relation between Th/U and the Pb loss, excluding an area in which $U^{238}$ elements are suddenly changed or gradually changed with an area in which the $U^{238}$ elements are stably distributed as an area designing LA-ICP-MS SPOT analysis spots, and designing an LA-ICP-MS spot analysis spot distribution diagram according to the above principle; and for the low-U minerals, searching for the compositional zonation having high U and low Pb, determining whether multiple stages exist, and designing an LA-ICP-MS spot analysis spot distribution diagram for an area in which $U^{238}$ elements are stably distributed and have a content greater than 10 ppm; and S6, accurately limiting a mineral formation age, which comprises the following sub-steps:

for the high-U minerals, processing and interpreting dating data by using ICPMSDataCal software, and drafting a U-Pb concordia diagram and a U-Pb weighted mean age diagram in combination with ISOPLOTR software; and for the low-U minerals, processing and interpreting data with the ICPMSDataCal software, and under the condition that single-spot $Pb^{206}/U^{238}$ age concordances are greater than 80%, drafting a U-Pb concordia diagram and a U-Pb weighted mean age diagram by using the ISOPLOTR software; and under the condition that most of single-spot $Pb^{206}/U^{238}$ age concordances are less than 80%, drafting Tera-Wasserburg U-Pb concordia diagrams with the ISOPLOTR software.

In one embodiment, the single mineral crystal in step S22 has a particle size greater than 0.1 mm.

In one embodiment, the laser ablation inductively coupled plasma mass spectrometer consists of an Agilent 7900 quadrupole plasma mass spectrometer, a COMPexPro 102 ArF 193 nm excimer laser and a MicroLas optical system; a U-Pb isotope is dated and contents of trace elements are processed with a mineral established standard sample and an international standard material glass standard sample NIST610 as calibration standards; and data are restored with iolite4 software and matrix data for mapping elements are exported.

In one embodiment, test parameters of the laser ablation inductively coupled plasma mass spectrometer include laser working parameters and ICP-MS working parameters; the laser working parameters are as follows: in a laser ablation process, high-purity helium is used as carrier gas and high-purity argon is used as compensation gas to adjust sensitivity, the high-purity helium and the high-purity argon are mixed by means of a T-shaped joint before entering plasma, mapping is used in an early stage, a sampling mode is rapid spot ablation, spots are connected to form a line, so as to form a plane, each analysis spot lasts for 3 s to 5 s, and includes a 1 s-2 s of blank signal and 2 s-3 s of sample ablation and cleaning time, a helium flow rate is 0.6 L/min-0.9 L/min, a laser energy density is 1.5 J/cm$^2$, a laser beam spot diameter is 5 μm-10 μm, a frequency is 10 Hz, and a scanning speed is 3 μm/s-6 μm/s; and the ICP-MS working parameters are as follows: radio frequency (RF) power is 1550 W, a plasma gas flow speed is 15 L/min, a sampling depth is 2 μm-5 μm, integration time is 2 s-5 s, and an auxiliary argon flow rate is 1.0 L/min.

In one embodiment, spot analysis is used in a later stage, a sampling mode is spot ablation, each analysis spot lasts for 70 s-90 s, and includes 15 s-20 s of blank signal, 40 s of sample ablation signal and 15 s-20 s of cleaning time, a helium flow rate is 0.8 L/min, laser energy is 80 mJ, a laser beam spot diameter is 32 μm-60 μm, a frequency is 2 Hz-8 Hz, and a pulse number is 90 times-200 times; and the ICP-MS working parameters are as follows: RF power is 1550 W, a plasma gas flow speed is 15 L/min, a sampling depth is 5 μm-5.5 μm, integration time is 40 s, and an auxiliary argon flow rate is 1.0 L/min.

In one embodiment, the K-means semi-automatic supervised multi-channel classification in step S3 is carried out with MATLAB software.

In one embodiment, the mineral phase separation in step S3 includes separating data minerals by means of contents of major elements of measured minerals, the major elements of the measured minerals are elements having contents greater than 5 wt. %, and only dating minerals are left while other minerals are removed, thereby obtaining a two-dimensional matrix image.

In one embodiment, in a specific implementation process of data cleaning and filtering analysis in step S4, data cleaning is carried out on the high-U minerals with the purified and separated high-U mineral data, the negative numbers and the null values are replaced with 0.1 time of a minimum value, median filtering is carried out on the processed data with MineralMAPPING software, and then the matrix data are converted into a two-dimensional element image with XMapTools software to highlight the element distribution law.

In one embodiment, data cleaning in step S4 is carried out on the low-U minerals by using the purified and separated low-U mineral data, the negative values and the null values are replaced with a value 0, median filtering is carried out on the processed data by using the MineralMAPPING software, and then the matrix data are converted into a two-dimensional element image by using the XMapTools software, and the compositional zonation having high $U^{238}$ and low $Pb^{204}$ is determined.

A second objective of the present disclosure is the use of the method for in-situ U-Pb dating of heterogeneous minerals in mineral exploration.

Compared with the prior art, the technical solutions of the present disclosure have the beneficial effects:

(1) The method for inverting an in-situ chronological history of heterogeneous minerals according to the present disclosure separates and purifies a target mineral by carrying out data analysis, extraction and enhancement on original mapping data, and further highlights distribution features of dating indexes (U content, Pb content, $Pb^{206}/U^{238}$ ratio, $Pb^{207}/U^{235}$ ratio and Th/U ratio) in a target mineral phase by using a noise data processing technology. It more intuitively displays a favorable dating portion and a crystal growth change trend of the dating mineral. A fine spot design for high-precision dating analysis in a later stage is provided. A plurality of geological events experienced by a heterogeneous mineral crystal in the growth process is accurately limited, so as to invert the mineral formation history which provides the basis for better study of mineralogy, mineral geochemistry and mineral geochronology. It is hence a novel indispensable auxiliary means of mineral geochronology and an auxiliary method for mineral exploration.

(2) The present disclosure accurately separates and purifies the target mineral by using a nonlinear smooth filtering technology by means of a K-means semi-automatic supervised multi-channel classification model. A connection between mapping data and spot data is hence established. The steps can be implemented by means of software MineralMAPPING. The method achieves use of the mapping data in in-situ dating of the heterogeneous minerals. The mapping data and the spot data are enhanced. The method has extremely strong practical and study value in the field of mineralogy, a mineral deposit and even geoscience.

(3) The method according to the present disclosure separates and purifies a heterogeneous dating mineral phase.

(4) Mapping analysis of the target mineral is achieved, and dating indexes in the target mineral are enhanced.
(5) A determination capability of dating mineral stages and precision set in high-precision dating spot are improved.
(6) The in-situ dating of the heterogeneous minerals is improved, and an evolution history of mineral crystals is inverted more accurately.
(7) The method for inverting an in-situ chronological history of heterogeneous minerals of the present disclosure can enhance geological information of mapping data, and more conveniently highlight chronology information of the dating mineral which is then inverted into the diagenetic and metallogenic history. It has great study significance and practical value.

BRIEF DESCRIPTION OF THE DRAWINGS

FIG. 6 is a graph showing results of LA-ICP-MS SPOT analysis data according to the Embodiment 1 of the present disclosure;
FIG. 14 is a graph showing results of LA-ICP-MS SPOT analysis data according to the Embodiment 2 of the present disclosure.

DETAILED DESCRIPTION OF THE EMBODIMENTS

Figure 1:
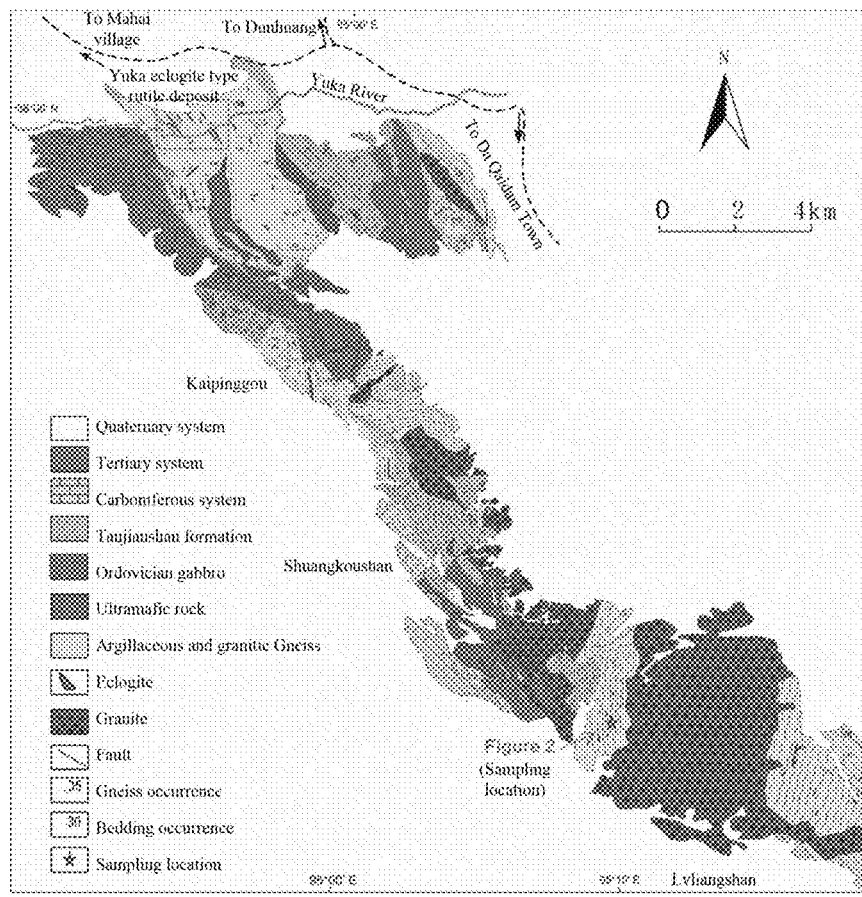
FIG. 1 is a map showing a favorable sampling section delineated in a north margin of a Qaidam basin.

If no specific technology or conditions are specified in the present disclosure, the present disclosure shall be carried out according to a technology or conditions described in the literature in the art or according to the product description. All of used reagents or instruments that are not specified by manufacturers are conventional commercially-available products.

Professional Terms and Technical Parameters Involved in the Present Disclosure (1) K-means semi-automatic supervised multi-channel classification: it is an iterative clustering analysis algorithm, and includes: pre-divide data into K groups, randomly select K objects as an initial clustering center, then compute a distance between each object and each seed clustering center, and assign each object to the clustering center closest to the object. The clustering centers and the objects assigned to the clustering centers represent a cluster. Each time a sample is assigned, the clustering center of the cluster is recomputed according to existing objects in the cluster. The process will continue being repeated until a certain termination condition is satisfied. The termination condition may be that no (or a minimum number) objects are reassigned to different clusters, no (or a minimum number) clustering centers are changed, and the sum of squared errors is locally minimized. A K-means algorithm defines a distance metric, which is represented by $d_{ij}$. A distance between a sample i and a sample j is $$d_{ij} = \sum_{k=1}^{p}(x_{ik} - x_{jk})^2 = \|x_i - x_j\|^2$$

to represent a square Euclidean distance. Specifically, p is a dimension of data (which is usually two dimensions). A K value is selected according to actual situations. In order to distinguish minerals studied from other minerals herein, the K value is generally selected as 2. A defined loss function is utilized to iterate and converge continuously to recompute a center of each cluster. The loss function is defined as the sum of a distance between the sample and a center of the cluster to which the sample belongs:

$$W(C) = \sum_{l=1}^{k} \sum_{C(i)=l} \|x_i - \bar{x}_l\|^2.$$

$\bar{x}_l = (\bar{x}_{1l}, \bar{x}_{2l}, \ldots \bar{x}_{pl})$ is a center of an l-th cluster.

(2) High-U minerals and low-U minerals: a threshold of a U content is set as 200 ppm herein. That is, minerals having the U content greater than or equal to 200 ppm are defined as the high U minerals, such as zircon, monazite and xenotime; and minerals having the U content between 1 ppm and 200 ppm are defined as low U minerals, such as rutile, apatite and garnet.
(3) Multiple stages: the multiple stages herein refer to significant differences in a U content, a Pb content, a $Pb^{206}/U^{238}$ ratio, a $Pb^{207}/U^{235}$ ratio and a Th/U ratio in heterogeneous minerals. By comparing a relation between an element content and a ratio of the minerals, the number of times of stages of formation events that the minerals have experienced is determined, and a mineral formation history is inverted.
(4) Median filtering: it is a sorting statistical theory based nonlinear signal processing technology that may effectively suppress noise. A principle thereof is to replace a value of a spot in a digital image or digital sequence with a median of a value of each spot in a neighborhood of the spot, so as to make surrounding pixel values approach to the value, thereby eliminating isolated noise spots. The median filtering is to remove a two-dimensional sliding template of a certain structure, sort pixels in the template according pixel values, and compute the median for replacement. An output of two-dimensional median filtering is g(x,y)=med({f(x−k,y−1), (k,1∈W)}). Specifically, f(x,y) and g(x,y) are an original signal and a processed signal respectively. Specifically, W is the two-dimensional template, and is usually a 3*3 area. Parameters of W may be adjusted according to specific situations.

(5) U-Pb concordia diagram: a $Pb^{206}/U^{238}$-$Pb^{207}/U^{235}$ coordinate map. According to a known age, a ratio is inversely computed, and spots are projected to obtain a curve representing a trajectory of a U-Pb system having consistent ages, i.e. a concordance line. A formed map is referred to as a concordance map. A specific style is shown in the examples.

(6) U-Pb weighted mean age diagram: a weighted mean age is computed according to $t_{average}=\Sigma(t_i/s[t_i]^2)/\Sigma(1/s[t_i]^2)$ with a $Pb^{206}/U^{238}$ age $(t_i)$ and error $(s[t_i])$ data of the age, and a diagram presented by the $Pb^{206}/U^{238}$ age $(t_i)$ and the error $(s[t_i])$ data of the age in a form of a box graph is the U-Pb weighted mean age map. A size of the weighted mean age not only depends on variation between ages of single zircon, but also depends on a number of times of occurrences of each zircon age. Generally, data having a concordance less than 80% are not used, and a specific style is shown in examples.

(7) Tera-Wasserburg U-Pb concordia diagrams: $Pb^{206}/U^{238}$-$Pb^{207}/Pb^{206}$ coordinate map. A trajectory formed by different time concordance age spots is referred to as a Tera-Wasserburg concordance curve. On the curve, a degree of concordance of relatively young minerals may be fully displayed. Generally, an age of a lower intersection spot is taken as an age of mineral formation.

MineralMAPPING software used in the present disclosure is independently developed by the applicant, and a computer software copyright registration certificate is 2020SR0341873.

Mapping analysis in the present disclosure is completed by a laser ablation inductively coupled plasma mass spectrometer. The laser ablation inductively coupled plasma mass spectrometer consists of an Agilent 7900 quadrupole plasma mass spectrometer, a COMPexPro 102 ArF 193 nm excimer laser and a MicroLas optical system. A U-Pb isotope is dated and contents of trace elements are processed with a mineral established standard sample and an international standard material glass standard sample NIST610 as calibration standards. Data are restored with iolite4 software and matrix data for mapping elements are exported.

Test parameters of the laser ablation inductively coupled plasma mass spectrometer include laser working parameters and ICP-MS working parameters. The laser working parameters are as follows: in a laser ablation process, high-purity helium is used as carrier gas and high-purity argon is used as compensation gas to adjust sensitivity, the high-purity helium and the high-purity argon are mixed by means of a T-shaped joint before entering plasma, mapping is used in an early stage, a sampling mode is spot ablation, each analysis spot lasts for 70 s, and includes a 15 s-20 s of blank signal and 40 s of sample ablation signal and 15 s-20 s of cleaning time, a helium flow rate is 0.8 L/min, laser energy is 80 mJ, a laser beam spot diameter is 44 μm, a frequency is 5 Hz, and a pulse number is 300 times. The ICP-MS working parameters are as follows: radio frequency (RF) power is 1550 W, a plasma gas flow speed is 15 L/min, a sampling depth is 5 mm-5.5 mm, integration time is 40 s, and an auxiliary argon flow rate is 1.0 L/min.

A laser ablation system is provided with a signal smoothing device. A laser beam spot and a step size of this analysis are 5 μm×5 μm, and ablation duration of each spot is 3 s. In U-Pb isotope dating and trace element content processing, a mineral established standard sample (for example, Zircon is calibrated by a 91500 standard sample) and a glass standard material NIST610 are used as external standards for fractionation correction of isotopes and trace elements respectively. In a later stage, data are restored with the iolite4 software and the matrix data of mapping elements are exported.

Embodiment 1

Inversion of In-Situ Chronological History of Low-U Heterogeneous Minerals (1) Systematically collect existing data of a stratum, a structure and magmatic rock in a North Qaidam, comprehensively analyze study potential of the North Qaidam, and systematically study and delineate a favorable sampling section, i.e. Lvliangshan study area, as shown in FIG. 1.

(2) Select a Lvliangshan area, and collect surface eclogite, i.e. felsic vein body sample; and in a sampling process, faithfully record the following information in detail, as shown in Table 1:

TABLE 1

| Sampling No. | Borehole No. | X | Y | Lithology | Occurrence | Symbolic mineral | Photograph | Location |
|---|---|---|---|---|---|---|---|---|
| 1 | | 365417 | 3275439 | Retrograde eclogite | Block shape | Rutile | ZP03 | Surface |
| 2 | TC201 | 365450 | 3275441 | Felsic vein | Block shape | Rutile | ZP04 | Trial trench |
| 3 | TC101 | 365465 | 3275413 | Felsic vein | Veined, 172∠65 | Rutile | ZP07 | Trial trench |

Figure 2:
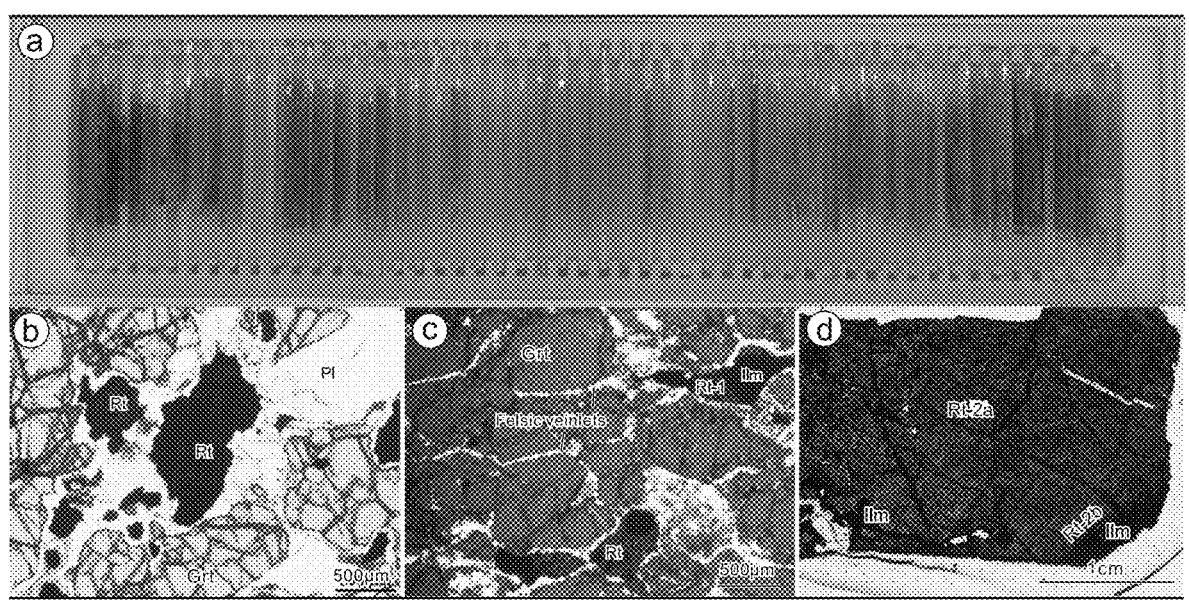
FIG. 2 is an image showing a rutile probe piece and microscopic petrographic features in a Lvliangshan area.

(3) Grind the collected bedrock sample into a probe piece and a laser sheet, microscopically observe microscopic petrographic features of rutile, and detailedly describe and record optical features, paragenetic association and special phenomena of the rutile; and select the rutile having representative features, and mark a location and cataloging a number (as shown in FIG. 2) on a probe piece or a laser sheet for accurate rutile minerals with a marking pen, and carry out in-situ element mapping analysis on a selected experimental test location by LA-ICP-MS.

Figure 3:
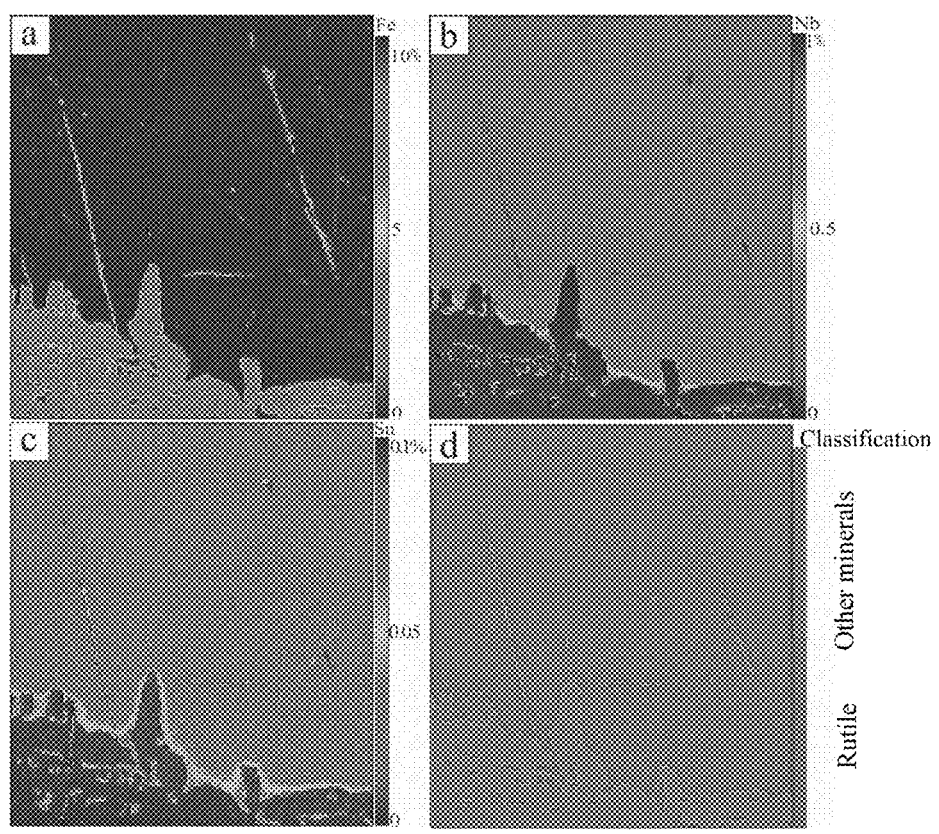
FIG. 3 shows (a-c) a mapping data set configured to perform classification and (d) a mineral phase separation effect according to Embodiment 1 of the present disclosure.

(4) Select Fe, Nb and Sn elements in LA-ICP MS mapping data as a classification basis (as shown in FIGS. 3a-3c), set a classification quantity into two categories by K-means semi-automatic supervised multi-channel classification, achieve phase separation of rutile from other minerals, and purify a rutile crystal (as shown in FIG. 3d).

Figure 4:
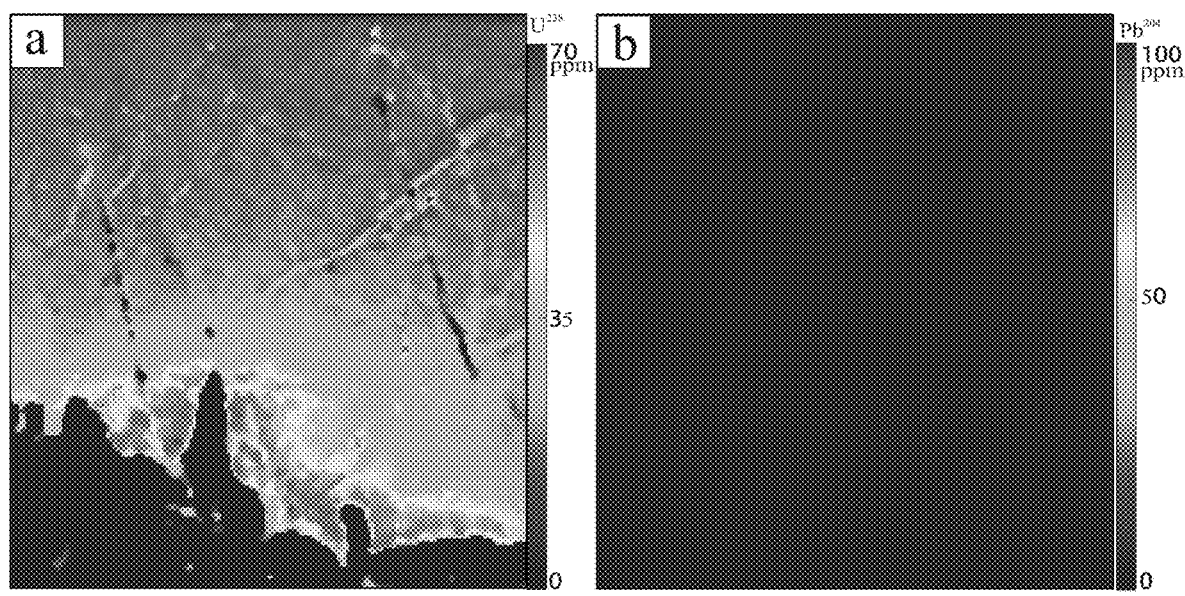
FIG. 4 shows a compositional zonation having high U238 and low Pb204 after median filtering according to the Embodiment 1 of the present disclosure.

(5) Re-sample purified and separated rutile data, replace negative values and null values, carry out median filtering on processed data, and determine a compositional zonation having high $U^{238}$ and low $Pb^{204}$ (as shown in FIG. 4), so as to make preparations for genetic determination and LA-ICP-MS spot analysis spot design of single minerals.

Figure 5:
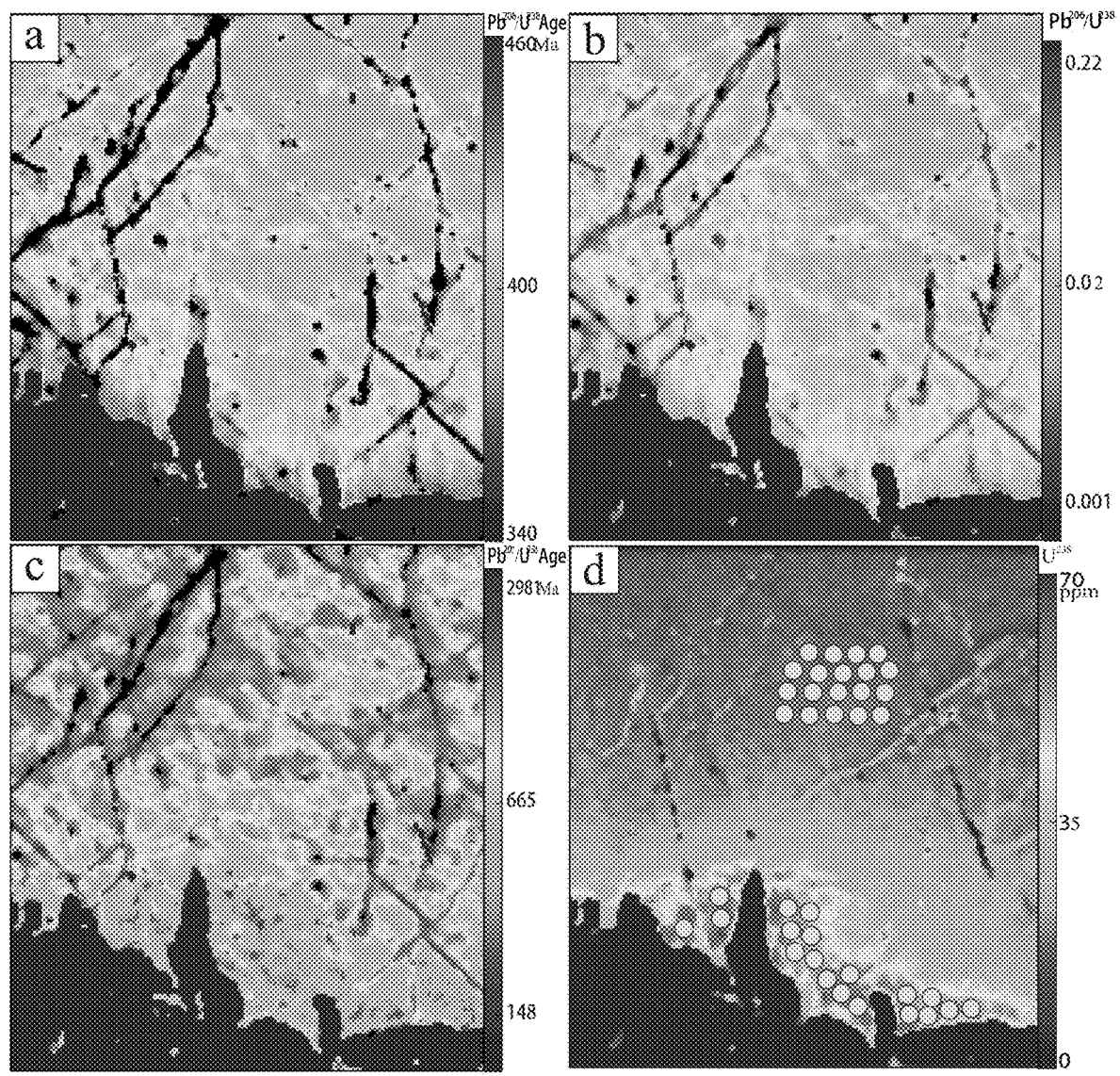
FIG. 5 is an image showing a rutile isotope ratio mapping multi-stage formation zonation and spot design according to the Embodiment 1 of the present disclosure.

(6) Search for the compositional zonation having high U and low Pb, a $Pb^{206}/U^{238}$ ratio and a $Pb^{207}/U^{235}$ ratio, determine whether multiple stages exist (FIGS. 5a-5c), design an LA-ICP-MS spot analysis spot distribution diagram (FIG. 5d), and carry out spot experiment test. LA-ICP-MS SPOT analysis data results are shown in FIG. 6.

Figure 7:
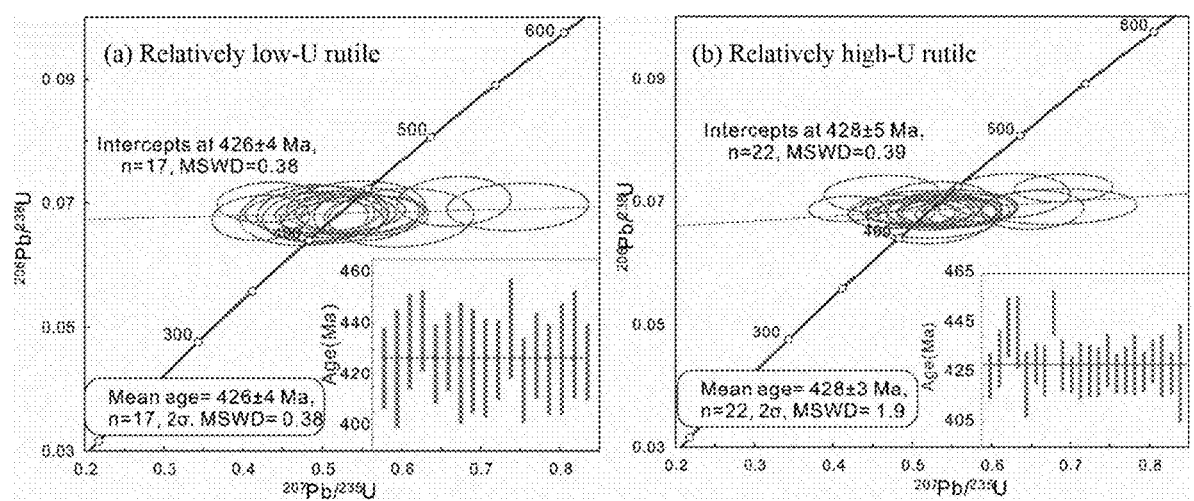
FIG. 7 shows (a) a rutile multi-stage SPOT high-precision U-Pb concordia diagram and (b) a U-Pb weighted mean age diagram according to the Embodiment 1 of the present disclosure.

(7) Process and interpret data by using ICPMDataCal software. It is found that single-spot $Pb^{206}/U^{238}$ age concordances are all greater than 80%, and therefore a U-Pb concordia diagram (as shown in FIG. 7a) and a U-Pb weighted mean age diagram (as shown in FIG. 7b) are manufactured with ISOPLOTR software. Therefore, it is found that there are two stages of U element enrichment in a growth process of a rutile crystal, which is highly enriched at 428 Ma in an early stage. With growth of the crystal, an enrichment degree is reduced at 426 Ma, such that an in-situ chronological history of heterogeneous minerals (Rutile) is inversed finely.

Embodiment 2

Inversion of In-Situ Chronological History of High-U Heterogeneous Minerals (1) Systematically collect existing data of a stratum, a structure and magmatic rock in a North Qaidam, comprehensively analyze study potential of the North Qaidam, and systematically study and delineate a favorable sampling section, i.e. Lvliangshan study area (as shown in FIG. 1).

Figure 8:
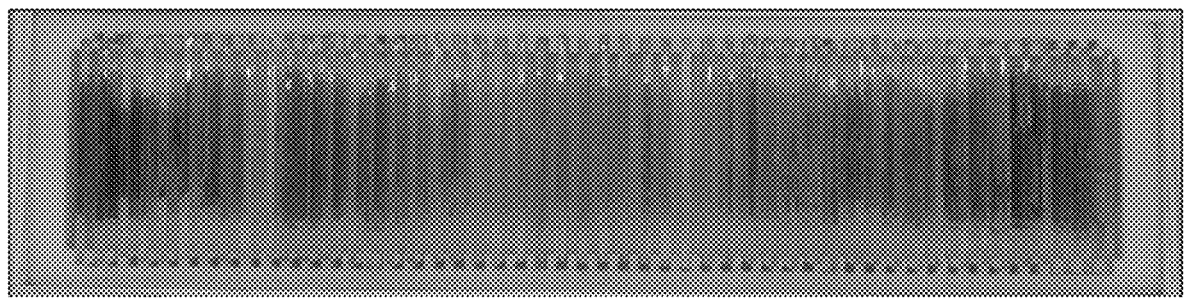
FIG. 8 is an image showing a zircon probe piece in a Lvliangshan area.

(2) Select a Lvliangshan area, and collect surface eclogite, i.e. felsic vein body sample; and in a sampling process, faithfully record the following information in detail, as shown in Table 2:

(3) Grind the collected bedrock sample into a probe piece and a laser sheet (as shown in FIG. 8), microscopically observe microscopic petrographic features of zircon, and detailedly describe and record optical features, paragenetic association and special phenomena of the zircon; and select the zircon having representative features, and mark a location and cataloging a number on a probe piece or a laser sheet for accurate zircon minerals with a marking pen, and carry out in-situ element mapping analysis on a selected experimental test location by LA-ICP-MS.

Figure 9:
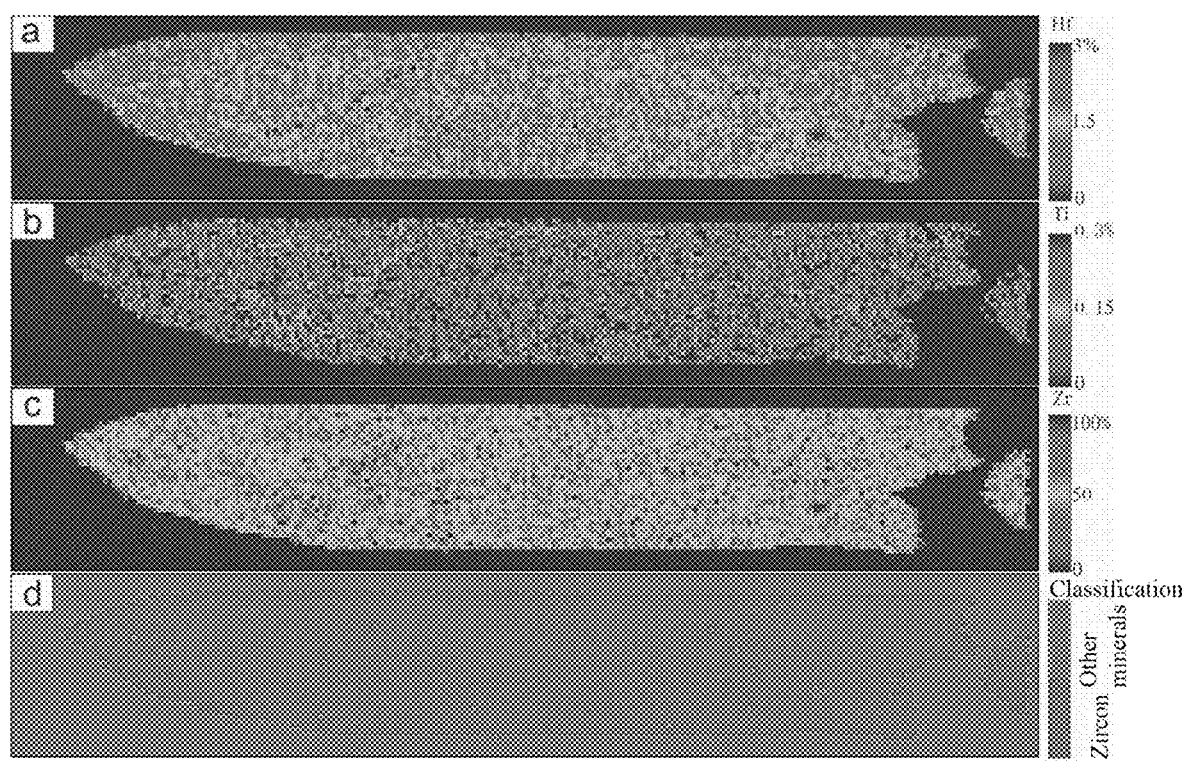
FIG. 9 shows (a-c) a mapping data set configured to perform classification and (d) a mineral phase separation effect according to Embodiment 2 of the present disclosure.

(4) Select Hf, Ti and Zr elements in LA-ICP MS mapping data as a classification basis (FIGS. 9a-9c), set a classification quantity into two categories by K-means semi-automatic supervised multi-channel classification, achieve phase separation of zircon from other minerals, and purify a zircon crystal (FIG. 10d).

Figure 10:
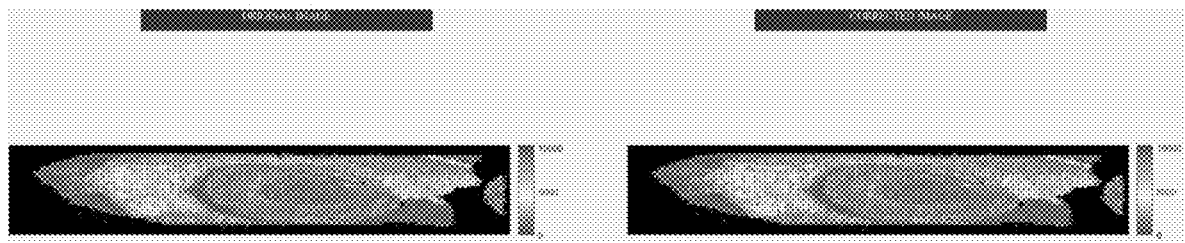
FIG. 10 is an image showing resampling and data preprocessing of purified mapping data according to the Embodiment 2 of the present disclosure.
Figure 11:
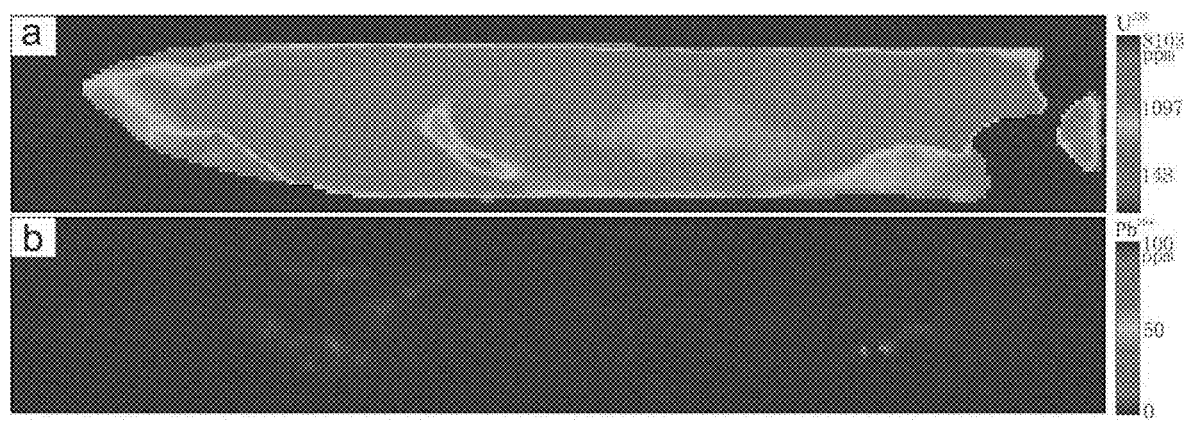
FIG. 11 is an image showing a compositional zonation having high U238 and low Pb204 after median filtering according to the Embodiment 2 of the present disclosure.

(5) Re-sample purified and separated zircon data, replace negative values and null values (as shown in FIG. 10), carry out median filtering on processed data, and determine a compositional zonation having high $U^{238}$ and low $Pb^{204}$ (as shown in FIG. 11) to highlight element zonation information, so as to make preparations for genetic determination and LA-ICP-MS spot analysis spot design of single minerals.

Figure 12:
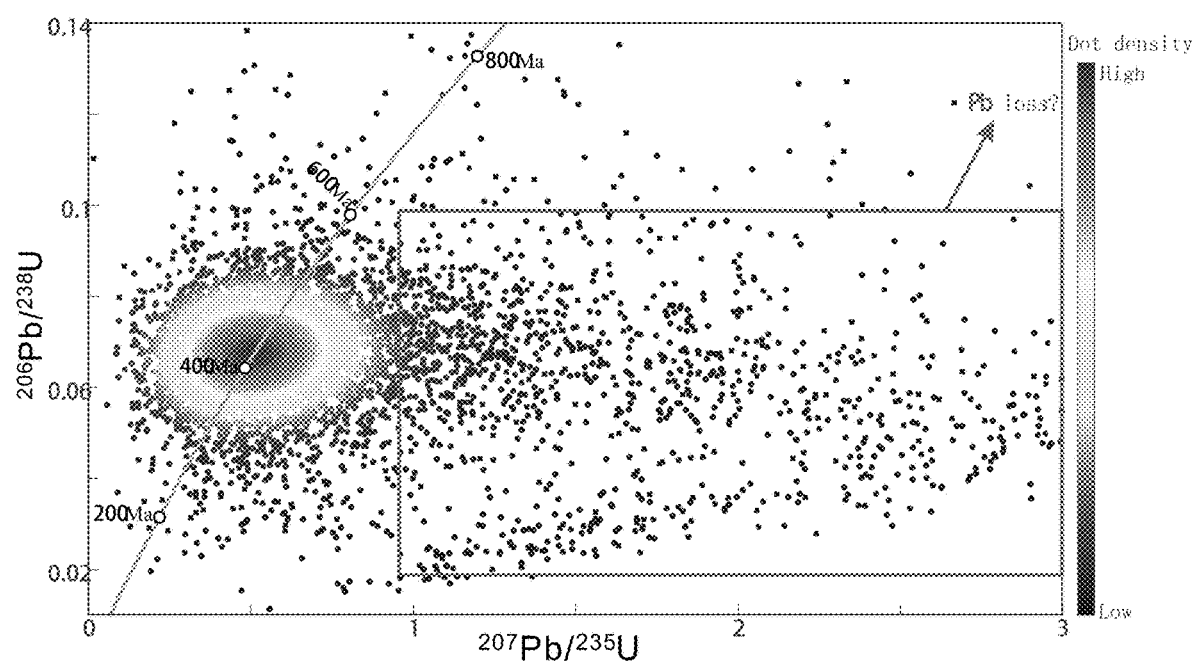
FIG. 12 is a graph showing a zircon isotope ratio mapping multi-stage formation zonation and spot design.
Figure 13:
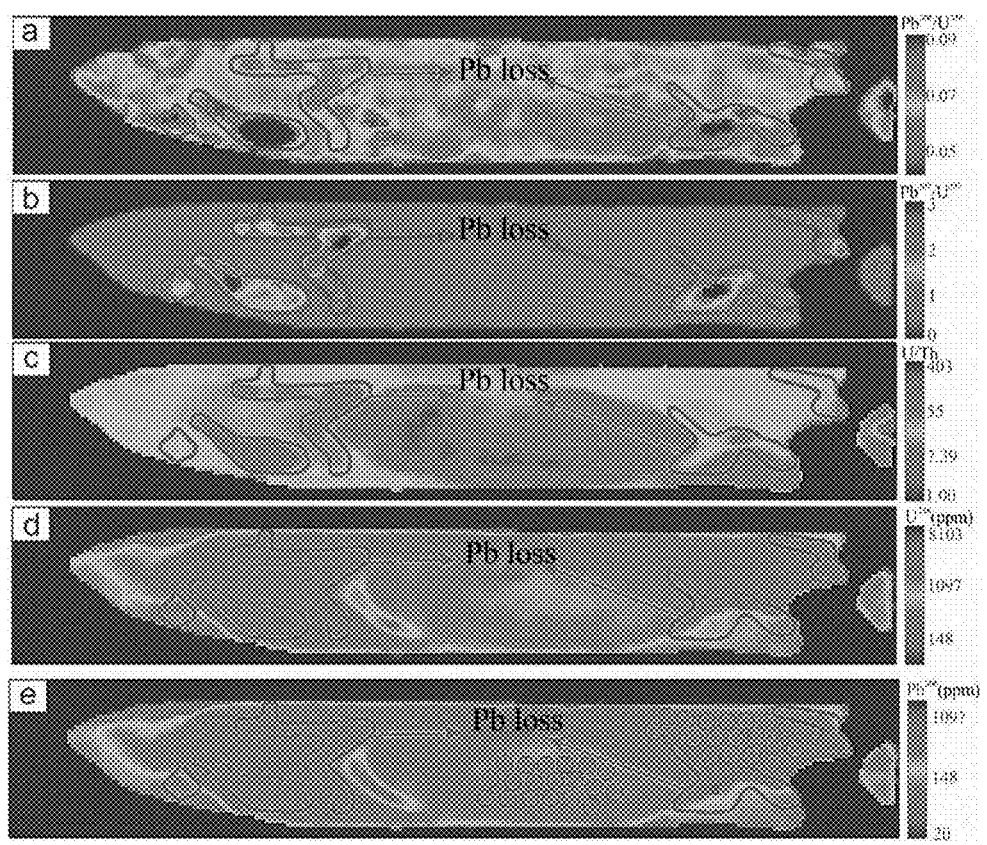
FIG. 13 is an image showing a zircon isotope ratio mapping multi-stage formation zonation, Pb loss and spot design.

(6) Draft a U-Pb concordia diagram (as shown in FIG. 12) with filtered data, search for the compositional zonation (as shown in FIGS. 13a-13b) having high U and low Pb, a $Pb^{206}/U^{238}$ ratio and a $Pb^{207}/U^{235}$ ratio, determine whether multiple stages and Pb loss exist (as shown in FIGS. 13a-13b), compute a relation (as shown in FIG. 13c) between Th/U and the Pb loss, design an LA-ICP-MS spot analysis spot distribution diagram (as shown in FIGS. 13d-13e), and carry out SPOT experiment test. LA-ICP-MS SPOT analysis data results are shown in FIG. 14.

Figure 15:
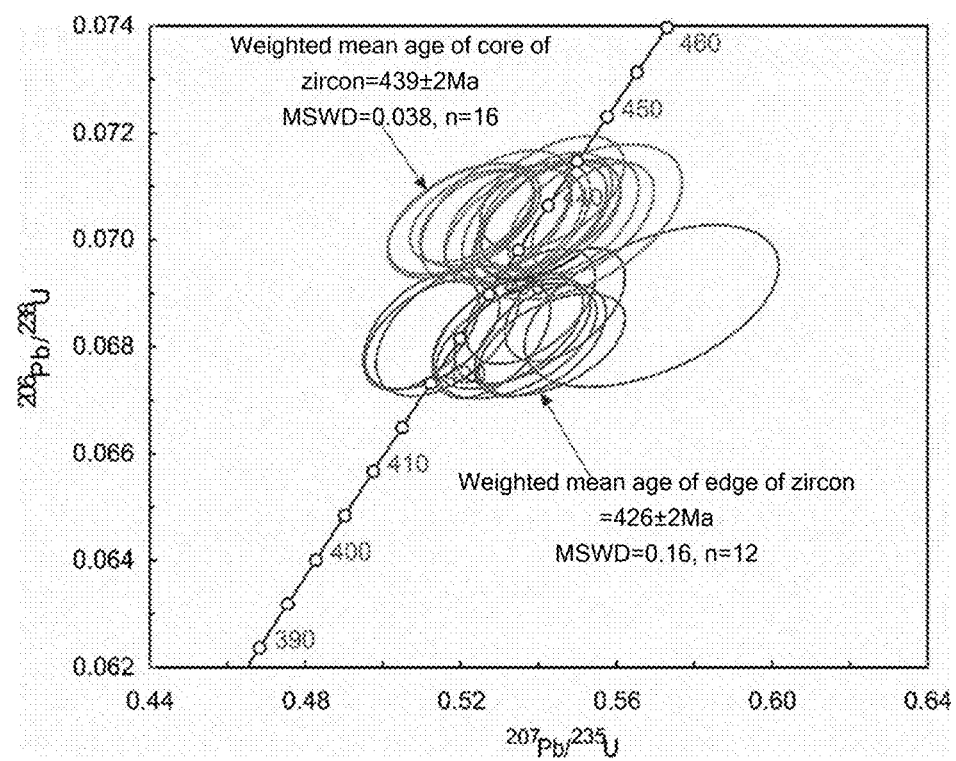
FIG. 15 is a zircon multi-stage SPOT high-precision U-Pb concordia diagram.

(7) Process and interpret data by using ICPMDataCal software, and draft a U-Pb concordia diagram (as shown in FIG. 15) and a U-Pb weighted mean age diagram with ISOPLOTR software. Therefore, it is found that there are multiple stages of crystal growth phenomena in zircon. A core of zircon is formed at around 439 Ma and formed in an environment having a high U/Th ratio. With long growth of a zircon crystal, an edge of the zircon is formed at around 426 Ma and formed in an environment with low U/Th ratio. In such an environment, a phenomenon of Pb loss exists due to geological events in a later stage, which is not conducive to determination of an age of the zircon. In the method, the in-situ chronological history and formation conditions of heterogeneous minerals (zircon) are finely inverted.

The above embodiments and the features in the embodiments herein can be combined with each other without conflict.

TABLE 2

| Sampling No. | Borehole No. | X | Y | Lithology | Occurrence | Symbolic mineral | Photograph | Location |
|---|---|---|---|---|---|---|---|---|
| 1 |  | 365477 | 3275489 | Retrograde eclogite | Block shape | Zircon | ZP01 | Surface |
| 2 | TC301 | 365410 | 3275491 | Felsic vein | Nervation | Zircon | ZP06 | Trial trench |
| 3 | TC201 | 365865 | 3275998 | Felsic vein | Nervation | Zircon | ZP08 | Trial trench |

What are described above are merely preferred embodiments of the present disclosure, and are not intended to limit

What is claimed is:

1. A method for in-situ U-Pb dating of heterogeneous minerals, comprising:
   S1, collecting a bedrock sample, wherein the bedrock sample is rich in any one of zircon, rutile or garnet;
   S2, carrying out petrographic analysis of the sample comprising the following sub-steps:
   S21, grinding the collected bedrock sample into a probe piece having a width of 25 mm, a length of 30 mm-35 mm and a thickness of 0.05 mm and a laser sheet having a width of 25 mm, a length of 30 mm-35 mm and a thickness of 0.08 mm, microscopically observing mineral features corresponding to the probe piece and the laser sheet, and recording petrography and paragenetic association features of the probe piece and the laser sheet;
   S22, selecting a single mineral crystal having a desirable crystal form, complete particles and no impurity inclusion as a sample; and
   S23, designing a rectangular area greater than a particle size of the single mineral crystal as an experimental test location with the single mineral crystal as a target on the bedrock sample, marking the rectangular area with a marking pen, and carrying out in-situ element mapping analysis on the selected experimental test location by a laser ablation inductively coupled plasma mass spectrometer;
   S3, carrying out mineral phase separation and purification based on mapping data comprising the following sub-steps:
   classifying matrix data of Laser Ablation Inductively Coupled Plasma Mass Spectrometry (LA-ICP-MS) mapping obtained in step S23 by K-means semi-automatic supervised multi-channel classification, and hence achieving mineral phase separation to purify the single mineral crystal;
   S4, carrying out data cleaning and filtering analysis comprising the following sub-steps:
   for high-U minerals, carrying out data cleaning with purified and separated high-U mineral data, negative numbers and null values are replaced with 0.1 time of a minimum value, median filtering is carried out on processed data with MineralMAPPING software, and then the matrix data are converted into a two-dimensional element image with XMapTools software to highlight an element distribution law; and
   for low-U minerals, carrying out data cleaning with purified and separated low-U mineral data, negative values and null values are replaced with a value 0, median filtering is carried out on processed data with the MineralMAPPING software, then the matrix data are converted into a two-dimensional element image with the XMapTools software, and a compositional zonation having high $U^{238}$ and low $Pb^{204}$ is determined; and
   S5, carrying out stage determination and spot design comprising the following sub-steps:
   for the high-U minerals, drafting a U-Pb concordia diagram with filtered data, determining whether multiple stages and Pb loss exist, computing a relation between Th/U and the Pb loss, excluding an area in which $U^{238}$ elements are suddenly changed or gradually changed with an area in which the $U^{238}$ elements are stably distributed as an area designing LA-ICP-MS SPOT analysis spots, and designing an LA-ICP-MS spot analysis spot distribution diagram according to the above principle; and
   for the low-U minerals, searching for the compositional zonation having high U and low Pb, determining whether multiple stages exist, and designing an LA-ICP-MS spot analysis spot distribution diagram for an area in which $U^{238}$ elements are stably distributed and have a content greater than 10 ppm; and
   S6, accurately limiting a mineral formation age comprising the following sub-steps:
   for the high-U minerals, processing and interpreting dating data by using ICPMSDataCal software, and drafting a U-Pb concordia diagram and a U-Pb weighted mean age diagram in combination with ISOPLOTR software; and
   for the low-U minerals, processing and interpreting data by using the ICPMSDataCal software, and under the condition that single-spot $Pb^{206}/U^{238}$ age concordances are greater than 80%, drafting a U-Pb concordia diagram and a U-Pb weighted mean age diagram by using the ISOPLOTR software; and under the condition that most of single-spot $Pb^{206}/U^{238}$ age concordances are less than 80%, drafting a Tera-Wasserburg U-Pb concordia diagram with the ISOPLOTR software.

2. The method according to claim 1, wherein the single mineral crystal in step S22 has a particle size greater than 0.1 mm.

3. The method according to claim 1, wherein the laser ablation inductively coupled plasma mass spectrometer comprises an Agilent 8900 quadrupole plasma mass spectrometer, a COMPexPro 102 ArF 193 nm excimer laser and a MicroLas optical system, a U-Pb isotope is dated and contents of trace elements are processed with a mineral established standard sample and an international standard material glass standard sample NIST610/NIST612 as calibration standards, and data are restored with iolite4 software and matrix data for mapping elements are exported.

4. The method according to claim 3, wherein test parameters of the laser ablation inductively coupled plasma mass spectrometer comprise laser working parameters and ICP-MS working parameters, wherein the laser working parameters are as follows: in a laser ablation process, high-purity helium is used as carrier gas and high-purity argon is used as compensation gas to adjust sensitivity, the high-purity helium and the high-purity argon are mixed by means of a T-shaped joint before entering plasma, mapping is used in an early stage, a sampling mode is rapid spot ablation, spots are connected to form a line, so as to form a plane, each analysis spot lasts for 3 s to 5 s, and comprises a 1 s-2 s of blank signal and 2 s-3 s of sample ablation and cleaning time, a helium flow rate is 0.6 L/min-0.9 L/min, a laser energy density is 1.5 J/cm², a laser beam spot diameter is 5 μm-10 μm, a frequency is 10 Hz, and a scanning speed is 3 μm/s-6 μm/s; and the ICP-MS working parameters are as follows: radio frequency (RF) power is 1550 W, a plasma gas flow speed is 15 L/min, a sampling depth is 2 μm-5 μm, integration time is 2 s-5 s, and an auxiliary argon flow rate is 1.0 L/min.

5. The method according to claim 4, wherein spot analysis is used in a later stage, a sampling mode is spot ablation, each analysis spot lasts for 70 s-90 s, and comprises 15 s-20 s of blank signal, 40 s of sample ablation signal and 15 s-20 s of cleaning time, a helium flow rate is 0.8 L/min, laser energy is 80 mJ, a laser beam spot diameter is 32 μm-60 μm, a frequency is 2 Hz-8 Hz, and a pulse number is 90 times-200 times; and the ICP-MS working parameters are as follows: RF power is 1550 W, a plasma gas flow speed is 15 L/min, a sampling depth is 5 µm-5.5 µm, integration time is 40 s, and an auxiliary argon flow rate is 1.0 L/min.

6. The method according to claim 5, wherein the K-means semi-automatic supervised multi-channel classification in step S3 is carried out by using MATLAB software.

7. The method according to claim 6, wherein the mineral phase separation in S3 comprises separating different minerals by means of contents of major elements of measured minerals, wherein the major elements of the measured minerals are elements having contents greater than 5 wt. %, and only dating minerals are left while other minerals are removed, thereby obtaining a two-dimensional matrix image.

8. Use of the method according to claim 1 in mineral exploration.

* * * * *